United States Patent [19]

Dussart-Lermusiaux et al.

[11] Patent Number: 4,814,403
[45] Date of Patent: Mar. 21, 1989

[54] OLIGOMER COMPOSITIONS OF POLYARYLOXYPYRIDINES WITH ACETYLENIC END GROUPS, THEIR MANUFACTURE AND LATTICES OBTAINED BY THERMAL POLYMERIZATION THEREOF

[75] Inventors: Annie Dussart-Lermusiaux, Villeurbanne; Michel Senneron, Meylan; Guy Rabilloud, Grenoble; Bernard Sillion, Lyons, all of France

[73] Assignee: Centre d'Etude des Materiaux Organiques pour Technologies Avancees, Vernaison, France

[21] Appl. No.: 105,745

[22] Filed: Oct. 8, 1987

[30] Foreign Application Priority Data

Oct. 9, 1986 [FR] France ............................ 86 14090

[51] Int. Cl.$^4$ ............................................ C08F 26/06
[52] U.S. Cl. .................................... 526/265; 526/263; 546/14; 546/261
[58] Field of Search .................. 526/263, 265; 546/14, 546/261

[56] References Cited

FOREIGN PATENT DOCUMENTS 1527714 4/1968 France ............................... 546/261

Primary Examiner—Paul R. Michl
Assistant Examiner—Alex H. Walker
Attorney, Agent, or Firm—Millen & White

[57] ABSTRACT

Oligomer compositions of polyaryloxypyridine with acetylenic end groups are obtained by formation of an oligomer composition of polyaryloxypyridine with halogenated end groups from an alkaline diphenolate and a dihalogenopyridine, followed with an ethynylation reaction. The average polycondensation degree may range from 1 to 50. Theses compositions can be used to form cross-linked lattices by polyaddition of the ethynyl groups.

14 Claims, No Drawings

OLIGOMER COMPOSITIONS OF POLYARYLOXYPYRIDINES WITH ACETYLENIC END GROUPS, THEIR MANUFACTURE AND LATTICES OBTAINED BY THERMAL POLYMERIZATION THEREOF

The present invention relates to new oligomer compositions of polyaryloxypyridine having acetylenic functional end groups. It also concerns the thermal polymerization of these compositions and cross-linked lattices of polyaryloxypyridine formed during the polyaddition of ethynyl groups.

The compositions comprising essentially polyaryloxypyridine with acetylenic end groups according to the invention, may be used as binders for manufacturing composite materials such as adhesives, coating varnishes and other raw materials for molded articles and cellular materials.

BACKGROUND OF THE INVENTION

The search for new thermostable thermosetting polymers by addition reactions which do not produce volatile compounds during their progress are of high interest for manufacturing dense, homogeneous materials of low porosity. For this purpose, polyaddition of acetylenic groups have already been used for cross-linking easily melted and soluble monomers or oligomers. As a matter of fact, these reactions take place by mere heating of the reactants with formation of dense and cross-linked systems.

Such addition reactions have been described with aromatic, aliphatic or arylaliphatic compounds containing amide, ester, ether, sulfone, ketone, imide, phenylene and quinoxaline chainings. These reactions have been disclosed for example in reviews by P. M. Hergenrother, J. Macromol, Sci. Rev. Macromol. Chem., 1980, C19, 1, by C. Y. Lee, I. J. Goldfarb, F. E. Arnold, T. E. Helminiak, A.C.S. Polymer Preprints, 1982, 24(2), 904 and 28th Natl. SAMPE Symposium, 1983, 699, by A. O. Hanky, Natl. SAMPE Symposium, 1983, 711 and by B. A. Reinhardt, G. A. Loughran, F. E. Arnold, Polym. Sci. Technol., 1984, 25, 40. Other examples of these reactions are for example found in U.S. Pat. Nos. 4,022,746, 4,098,767, 4,100,138, 4,131,625, 4,283,551 and Belgian patent No. 898,889.

One of the major difficulties frequently encountered with thermosetting resins involving oligomers with acetylenic end groups, is their melting or softening temperature which is mostly higher than the temperature at which polymerization of acetylenic groups takes place. As a matter of fact, it has been observed that the polymerization of these groups begins at relatively low temperature, generally lower than 200° C. Techniques of thermal analysis, differential calorimetry analysis and thermomechanical analysis show that the polymerization thermal threshold is often in the range from 120° C. to 180° C. In these conditions, it is preferable, for controlling the polymerization process, to use compositions having a melting or softening temperature substantially lower than the temperature prevailing at the beginning of the polymerization.

Aromatic polyethers, particularly those whose aromatic rings are interconnected through oxygen atoms in meta position, are known as having rather low melting temperatures since some of them are used as thermostable fluids. But the formation of ether bonds between aromatic carbon rings involved condensation reactions occurring at high temperature which requires the presence of catalytic systems essentially comprising copper.

Halogen atoms in ortho or para position from a heterocyclic nitrogen atom are known as being much more reactive than those fixed on the carbon atoms of a carbon ring. Among the nitrogenous heterocyclic compounds which have a high resistance to heat and oxidation, pyridine has the advantage of being industrially available. Accordingly, its derivatives with halogen on positions 2 and 4 or 2 and 6 constitute convenient raw materials for synthesizing oligomers of aromatic-heterocyclic polyethers.

OBJECTS OF THE INVENTION

One of the objects of the invention is to provide new compositions containing acetylenic groups, characterized by a relatively short gelation time at a temperature preferably lower than 250° C., under easier working conditions than with the resins of the prior art and giving finished products having good thermal and mechanical properties.

The present invention more particularly concerns the synthesis of new oligomer compositions of polyaryloxypyridine having acetylenic end groups. The polyaryloxypyridine resins with acetylenic end groups according to the invention have the exceptional advantage of being formed of polyaryloxypyridine whose melting or softening temperature is always lower than 200° C. As the ether chainings between the pyridine rings and the aromatic carbon rings are in meta position on pyridine, the polyaryloxypyridine oligomers according to the invention have highly remarkable properties of fusibility, solubility and flexibility.

Another object of the invention relates to the cross-linked products obtained during the reactions of polyaddition of acetylenic end groups, i.e the lattices formed during the thermal polymerization of these groups. These lattices are characterized by a very high thermal stability and a high resistance to oxidation.

SUMMARY OF THE INVENTION

The invention is more particularly concerned with oligomer compositions of polyaryloxypyridine with acetylenic end groups which comply with the general formula:

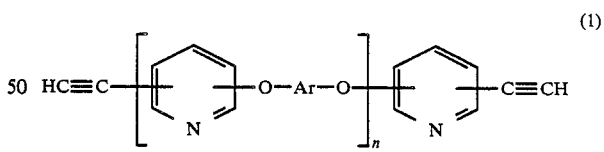

(1)

In this formula, radical Ar is a divalent carbocyclic or heterocyclic aromatic radical, the two valences of which are on separate carbon atoms. Radical Ar may be formed of one or more rings which are either fused or interconnected, each ring being formed preferably of 5-7 atoms, a part of which may be oxygen, sulfur and/or nitrogen atoms.

When radical Ar comprises several interconnected rings, the linking elements are for example the single bond or one of the following atoms or groups: $-O-$; $-S-$; $-SO-$; $-SO_2-$; $-CH_2-$; $-C(CH_3)_2-$; $-CO-$; $-CHOH-$; $-COO-$; $-CONH-$; $-Si(CH_3)_2-$; $-Si(CH_3)_2-O-Si(CH_3)_2-$.

The linking elements may also be partially or completely fluorinated hydrocarbon divalent radicals of the aliphatic, arylaliphatic or cycloaliphatic type, preferably containing 1 to 10 carbon atoms.

The ether bonds between radical Ar and the pyridine ring are shown at the middle of the latter to represent isomer existence depending on the position (2, 4 or 6) of the pyridine carbon atom onto which the bonds are fixed.

n is a number indicating the average polycondensation degree. It may for example range from 1 to 50. Number n is not always directly accessible, but its average value is deduced from the respective molar proportions of the reactants used to prepare the polyaryloxypyridine oligomer compositions.

The general method of synthesizing the composition of general formula (1) involves ethynylating an oligomer composition of polyaryloxypyridine having halogenated end groups which may be represented by general formula:

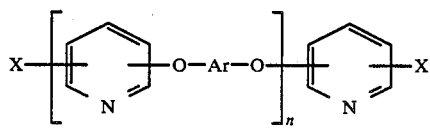   (2)

with compounds carrying an acetylene group, of general formulas:

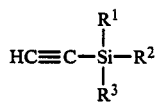   (3)

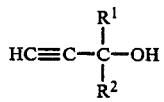   (4)

In these formulas, X is a halogen atom, preferably bromine or chlorine, Ar has the same meaning as above, $R^1$, $R^2$ and $R^3$, identical or different, are aliphatic or aromatic hydrocarbon monovalent remainders having 1 to 13 carbon atoms. More particularly convenient groups are methyl, ethyl, propyl, isopropyl, butyl, tert-butyl, vinyl, isopropenyl, phenyl or tolyl groups.

The oligomer compositions of polyaryloxypyridine with halogenated end groups of general formula (2) may be prepared by reacting a 2,6-dihalogenopyridine or a 2,4-dihalogenopyridine of formulas:

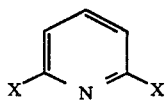   (5)

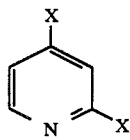   (6)

with an amount, in defect with respect to the molecular stoichiometry, of at least one diphenolate of general formula:

M—O—Ar—O—M   (7)

derived from the corresponding diphenol.

In these formulas, X and Ar have the above-mentioned meaning and M is an atom of alkali metal, preferably sodium or potassium.

Particularly convenient diphenols according to the invention are for example: 1,2-dihydroxybenzene, 1,3-dihydroxybenzene, 1,4-dihydroxybenzene, dihydroxytoluenes, dihydroxyxylenes, dihydroxynaphthalenes, 2,2'-dihydroxybiphenyl, 3,3'-dihydroxybiphenyl, 4,4'-dihydroxybiphenyl, bis(3-hydroxyphenyl)methane, bis(4-hydroxyphenyl)methane, bis(3-hydroxyphenyl)ether, bis(4-hydroxyphenyl)ether, bis(3-hydroxyphenyl)sulfide, bis(4-hydroxyphenyl)sulfide, bis(3-hydroxyphenyl)sulfone, bis(4-hydroxyphenyl)sulfone, bis(3-hydroxyphenyl)sulfoxide, bis(4-hydroxyphenyl)sulfoxide, 3,3'-dihydroxybenzophenone, 4,4'-dihydroxybenzophenone, bis 2,2-(4-hydroxyphenyl)propane, bis 2,2-(4-hydroxyphenyl)1,1,1,3,3,3-hexafluoropropane, bis(3-hydroxyphenyl)dimethylsilane, bis(4-hydroxyphenyl)dimethylsilane, bis 1,3-(3-hydroxyphenyl)1,1,3,3-tetramethyl disiloxane, and bis 1,3-(4-hydroxyphenyl)1,1,3,3-tetramethyl disiloxane.

Dihalogenopyridines particularly useful according to the invention are: 2,6-difluoropyridine, 2,6-dichloropyridine, 2,6-dibromopyridine, 2,6-diiodopyridine, 2,4-difluoropyridine, 2,4-dichloropyridine, 2,4-dibromopyridine and 2,4-diiodopyridine.

Compositions of general formula (1) are prepared in two successive main steps with separation of the intermediary compounds, these two steps being: (a)-the preparation of oligomers of polyaryloxypyridine with halogen end groups of formula (2), and (b)-the ethynylation of said compositions by substituting to halogen atoms an acetylenic compound having one of its reactive sites protected by a protecting group, this reaction being performed in the presence of a catalytic system, and then unblocking the blocked acetylenic function.

In the first step, the compositions of polyaryloxypyridine with halogen end groups (2) are prepared in two successive reactions with or without separation of intermediary compounds.

In the first reaction, a diphenol is converted to an alkaline diphenolate of formula (7) by reaction with an alkali metal, a hydroxide, a carbonate or an alcoholate of alkali metal. This reaction is performed according to well-known methods, preferably in solution in a polar organic solvent to which an aliphatic or aromatic hydrocarbon may be added for removing the reaction water, if any, by azeotropic distillation. It is always preferable to maintain the reaction medium proof against moisture.

In the second reaction, the dihalogenopyridine of formula (5) or (6) is added to the diphenolate (7), in molecular proportions always corresponding to a defect of the latter reactant. Thus, the molar proportion of diphenolate (7) to dihalogenopyridine (5) or (6) is generally from about 1/1.02 to ½, so as to obtain an oligomer composition of polyaryloxypyridine with halogen end groups of general formula (2) with a suitable average polycondensation degree (n from 1 to 50). This condensation reaction which leads to ether chainings is conducted by heating at a temperature from 50° to 300° C., preferably from 90° to 250° C. It may be performed at the reactant melting temperature, but it is preferable to use a polar organic solvent such for example as N-methyl pyrrolidone, dimethylsulfoxide, dimethylacetamide or dimethylformamide.

The second step involves a reaction of substitution of halogen end groups of polyaryloxypyridine compositions (2) with acetylenic compounds, having one of their reactive sites protected by a protecting group, said compounds complying with general formulas (3) and (4), followed with the removal of said protecting group.

The reaction of polyaryloxypyridines having halogen end groups (2) with acetylenic compounds (3) or (4) is preferably performed in solution in an organic solvent, in the presence of a basic compound liable to fix the halogen end atoms which are removed as a hydracid, and in the presence of a catalytic system comprising copper and palladium compounds with, optionally, a coordination agent. This reaction gives polyaryloxypyridines complying with the general formulas:

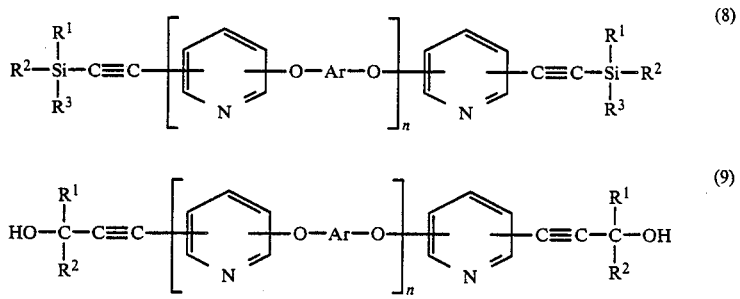

The substitution of halogen atoms with acetylenic compounds (4) or (5) is performed by heating at a temperature from 20° to 200° C., preferably 50° to 120° C., in solution in a solvent which may be an organic solvent inert with respect to the reaction products, but which may also be the basic compound used to fix the hydracid.

Polyaryloxypyridines with acetylenic end groups of formula (1) are obtained by disilylation of compositions of formula (8) or by removal of a ketone of the formula $R^1$—CO—$R^2$ in the compositions of formula (9).

Palladium compounds advantageously used in the catalytic system comprise, for example, compounds of general formulas: $Pd(PR_3)_4$, $Pd(PR_3)_2X_2$, $Pd(O_2CR)_2$, $Pd(O_2CR)_2(PR_3)_2$ and $Pd(AsR_3)_2X_2$, wherein X is a halogen atom and R an alkyl, aralkyl or aryl group. Examples of such compounds are: palladium acetate, palladium diacetato bis(triphenylphosphine), palladium dichloro bis(triphenylphosphine), palladium tetrakis(triphenylphosphine), palladium bis(1,2-bis(diphenylphosphino)ethane), and palladium dichloro bis(triphenylarsine).

Examples of copper compounds which can be used in the catalytic system are cuprous chloride, cuprous iodide, cuprous bromide, cuprous oxide and cuprous cyanide.

The coordination agents which can be added to the catalytic system are generally phosphorus, arsenic or antimony derivatives, as for example triphenylphosphine, tris(ortho-tolyl)phosphine, triphenylarsine and triphenylstibine.

The basic compounds, one object of which is to capture the hydracid molecules released during the reaction, are preferably amino compounds, including primary amines such as hexylamine, benzylamine and aniline, secondary amines such as dimethylamine, diethylamine, methylethylamine, N-methylaniline, N-ethylaniline, piperidine and tertiary amines such as trimethylamine, triethylamine, N,N-dimethylaniline, benzyldimethylamine and N,N,N',N'-tetramethyl ethylenediamine.

Amines having a boiling temperature ranging from 50° to 150° C. such as diethylamine, triethylamine and N,N,N',N'-tetramethylethylenediamine are particularly convenient.

The substitution of the halogen atoms of polyaryloxypyridine (2) with acetylenic compounds (3) or (4) may be performed in solution in one of the above-mentioned amine compounds, but it is also possible to add to the reaction medium another solvent which may be a hydrocarbon such for example as hexane or benzene, a halogenated hydrocarbon as dichloromethane or chloroform or an ether as diethyl ether, dibutyl ether, tetrahydrofuran, ethyl acetate or dioxane.

The desilylation reaction of polyaryloxypyridines of formula (8) is performed in solution in an aliphatic mono-alcohol such as methanol, ethanol, isopropanol or tert-butanol, in the presence of an inorganic base such as sodium hydroxide, potassium hydroxide, potassium carbonate or potassium fluoride, at a temperature preferably ranging from 50° to 150° C. and preferably in an inert atmosphere. This desilylation reaction may be performed by using exculusively as the solvent the monoalcohol, but it is also possible to add to the reaction medium an inert co-solvent such as diethyl ether, tetrahydrofuran or dioxane.

The removal of ketones from polyaryloxypyridines of formula (9) is performed in solution in an organic solvent which may be a hydrocarbon, an ether, an amide, an aldehyde, an alcohol or an ester, in the presence of an inorganic base such as sodium hydroxide or potassium hydroxide, at a temperature ranging from 50° to 150° C., preferably in an anhydrous medium and in an inert atmosphere.

The compositions consisting essentially of polyaryloxypyridines with acetylenic end groups according to the invention are thermosetting compositions. The reaction process whereby the fusible and soluble oligomers can be converted, by heating, to dense and cross-linked systems is not simple. Several polymerization and cyclotrimerization reactions are superposed, which finally lead to the cross-linked system.

Generally, the compositions according to the invention are polymerized by heating at a temperature from 100° to 250° C., for a time from a few minutes to a few hours. After the polymerization phase, the cross-linking degree may still be increased by a complementary thermal treatment at higher temperature, for example from 200° to 300° C.

By this operation, it is possible to continue in solid phase the polymerization reactions and to increase the vitrous transition temperature of the polymers by several tens of centigrade degrees.

The cross-linked polymers obtained by thermally polymerizing compositions of polyaryloxypyridine with acetylenic end-groups are characterized by an excellent behavior to heat and to oxidation. Thus, when the polymerization reaction is conducted at 180° C. for 2 hours, the isothermal thermogravimetry analysis, at 300° C. for 20 hours, shows that the weight loss of the most highly cross-linked systems is lower than 3%.

The invention also involves the compositions of polyaryloxypyridine oligomers with acetylenic end groups complying with the above-mentioned general formula (1), but wherein the ether chainings are placed on the carbon atoms in 3 and 5 positions of the pyridine rings. As a matter of fact, it has been discovered that, even though the activation effect of the halogen atoms placed in ortho or para position is higher than on the apices placed in meta position, the presence of the nitrogen atom in the heterocycle clearly facilitates the reactions of nucleophilic substitution onto the latter apices when compared to halogenated carbocyclic aromatic hydrocarbons. By using experimental conditions adapted to this difference of reactivity, it is thus possible to prepare polyaryloxypyridine compositions with halogen end groups by reacting an alkaline diphenolate with a 3,5-dihalogenopyridine.

The general synthesis process for these compositions is identical to that precedingly described.

It consists of first preparing compositions of polyaryloxypyridines with halogen end groups by reacting a 3,5-dihalogenopyridine with an amount lower with respect to the molecular stoichiometrical proportion, of at least one alkaline diphenolate.

Suitable 3,5 dihalogenopyridines are the 3,5-difluoro-, dichloro-, dibromo- and diiodo-pyridines.

The second step consists of substituting halogen end groups of said polyaryloxypyridine compositions with acetylenic compounds one of the reactive sites of which is protected by a protecting group, and then removing said protecting group. All these reactions have been described above.

It has been observed that the compositions of polyaryloxypyridines with acetylenic end groups, obtained with the use of 3,5-dihalogenopyridines, exhibit in certain respects improved characteristics as compared with compositions deriving from 2,4- and 2,6-dihalogenopyridines. In particular, they generally have a lower melting or softening temperature and a higher thermal stability. Hence, they will be more convenient for applications requiring an initial operation at lower temperature, while necessitating a high thermal stability of the final lattice.

EXAMPLES

The invention will be more precisely described in connection with the following specific examples wherein the details are given for illustrative but non limitative purpose. In these examples, the polycondensation reactions are conducted under stirring and in a nitrogen or argon inert atmosphere so as to avoid any oxidation reaction. The obtained products are characterized by elementary analysis, infra-red spectroscopy, nuclear magnetic resonance of the proton and of carbon 13, differential enthalpy analysis, steric exclusion chromatography and gel permeation chromatography. The polycondensation degree of polyaryloxypyridines is determined by gel permeation chromatography by determination of the halogen end groups proportion (proportion expressed as halogen weight per 100 grams of product), as well as by nuclear magnetic resonance.

EXAMPLE 1

A mixture of 59.2 grams (0.4 mole) of 2,6-dichloropyridine, 22 grams (0.2 mole) of 1.3-dihydroxybenzene, 41.49 grams of potassium carbonate, 110 cm$^3$ of N-methyl 2-pyrrolidinone and 75 cm$^3$ of toluene is heated for 7 hours at 130° C., with removal by azeotropic distillation of the water formed during the reaction. Toluene is then distilled and the solution is poured into one liter of water. The product which precipitates is washed with water, filtered and dried at 50° C. under reduced pressure.

The resultant product, which is obtained with a 90% yield (59.9 g), has a melting temperature of 81° C. This compound, whose molecular weight is 333 grams, is identified by analysis as bis 1,3-(2-chloro-6-pyridyloxy)-benzene complying with the formula:

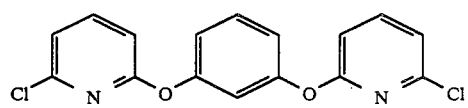

EXAMPLES 2 TO 8

A series of polyaryloxypyridines having halogen end groups is prepared according to the experimental conditions of example 1, with the reactants indicated in Table I.

TABLE I

| Example | Diphenol[1] | Dihalogeno pyridine | Yield (%) |
|---|---|---|---|
| 2 | R | 2,6-dibromo | 91 |
| 3 | A | 2,6-dichloro | 96 |
| 4 | A | 2,6-dibromo | 94 |
| 5 | F | 2,6-dibromo | 63 |
| 6 | S | 2,6-dibromo | 90 |
| 7 | A | 2,4-dibromo | 89 |
| 8 | A | 2,4-dichloro | 95 |

[1]Diphenols are as follows:
A: Bis 2,2-(4-hydroxyphenyl)propane
F: Bis 2,2-(4-hydroxyphenyl)1,1,1,3,3,3,propane
S: Bis (4-hydroxyphenyl)sulfide
R: 1,3-dihydroxybenzene (resorcinol)

The amounts used correspond to 0.4 mole of dihalogenopyridine, 0.2 mole of diphenol, 0.3 mole of potassium carbonate, 110 cm$^3$ of N-methyl 2-pyrrolidinone and 75 cm$^3$ of toluene. By chemical and spectroscopy analyses, the products formed in these reactions can be respectively identified as the following compounds.

EXAMPLE 2

Bis 1,3-(2-bromo 6-pyridyl oxy)benzene having a melting temperature of 93° C. and a molecular weight of 422 grams. This compound corresponds to the following chemical formula:

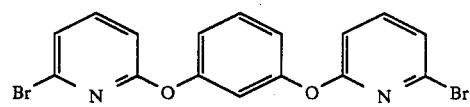

EXAMPLE 3

Bis 2,2-(4-(2-chloro 6-pyridyloxy)phenyl)propane having a melting point of 142° and a molecular weight of 451 grams and complying with the following formula:

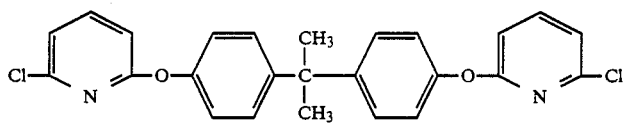

EXAMPLE 4

Bis 2,2-(4-(2-bromo 6-pyridyloxy)phenyl)propane having a melting point of 127° C. and a molecular weight of 540 grams, whose molecular formula is the following:

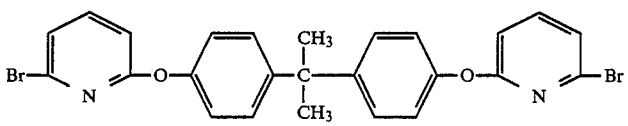

EXAMPLE 5

Bis 2,2-(4-(4-(2-bromo 6-pyridyloxy)phenyl)1,1,1,3,3,3-hexafluoropropane having a melting temperature of 120° C., a molecular weight of 648 grams and complying with the following formula:

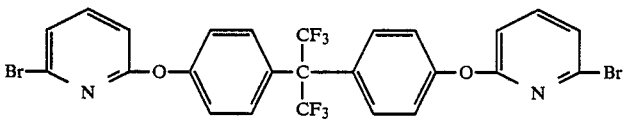

EXAMPLE 6

Bis(4-(2-bromo 6-pyridyloxy)phenyl)sulfide having a melting temperature of 82° C. and a molecular weight of 530 grams. This compound is represented by the following formula:

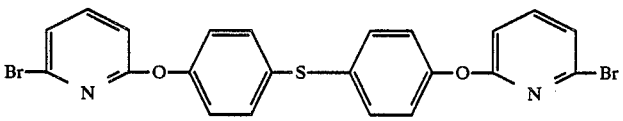

EXAMPLE 7

Chromatographic analysis shows that the obtained product is the mixture of three compounds which are probably the following: bis 2,2-(4-(2-bromo 4-pyridyloxy)phenyl)propane, bis 2,2(4-(4-bromo 2-pyridyloxy)phenyl)propane and 2,2-(4-(2-bromo 4-pyridyloxy)phenyl 4'-(4-bromo 2-pyridyloxy)phenyl)-propane.

EXAMPLE 8

As in example 7, the chromatographic analysis shows that the obtained product is also a mixture of two or three isomers.

EXAMPLE 9

A mixture of 11.4 grams (0.05 mole) of bis 2,2-(4-hydroxyphenyl)propane with 4 grams (0.1 mole) of sodium hydroxide, 17 cm$^3$ of dimethylsulfoxide and 10 cm$^3$ of toluene is heated for 4 hours at 120°-130° C., with removal of the water formed during the reaction by azeotropic distillation of the water-toluene mixture. Toluene is then completely distilled off before addition of 11.1 grams (0.075 mole) of 2,6-dichloropyridine. The etherification reaction is conducted by heating the reaction medium for 4 hours at 150° C. The cooled mixture is poured into a normal aqueous solution of sodium hydroxide. The formed precipitate is separated by filtration, washed with water, and dried to constant weight at 50° C. under reduced pressure. The resultant product, obtained with a yield of 97%, may be identified as a polyaryloxypyridine of formula:

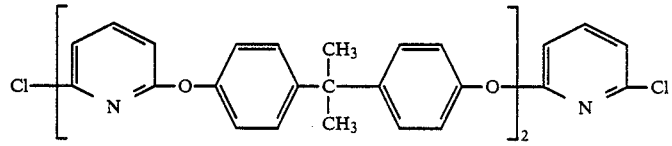

EXAMPLES 10 TO 15

A series of polyaryloxypyridines with halogen end groups, having a polycondensation degree ($\overline{DPn}$) ranging from 2 to 50, is prepared in the experimental conditions of example 9. The weight of dihalogenopyridine, indicated in grams in table 2, is reacted with 13.7 grams (0.06 mole) of bis 2,2-(4-hydroxyphenyl)propane and 4.8 grams (0.12 mole) of sodium hydroxide.

TABLE 2

| Example | 2,6-dichloro pyridine | 2,6-dibromo pyridine | DPn Calc[1] | DPn Found[2] |
|---|---|---|---|---|
| 10 | | 18.95 | 3 | 2.5 |
| 11 | 10.66 | | 5 | 2.5 |
| 12 | | 16.58 | 6 | 5.92 |
| 13 | 9.77 | | 10 | 3.6 |
| 14 | | 15.16 | 15 | 9.2 |
| 15 | | 14.50 | 50 | 20.3 |

[1]calculated from the respective proportions of dihalogenopyridine and of diphenol.
[2]found by quantitative elementary analysis of halogen atoms.

Depending on the selection of the starting product as 2,6-dibromopyridine or 2,6-dichloropyridine, the polymers prepared in examples 10 to 15 comply with the following formula wherein X is the halogen atom (bromine or chlorine) and n has the value indicated for $\overline{DPn}$ in table 2.

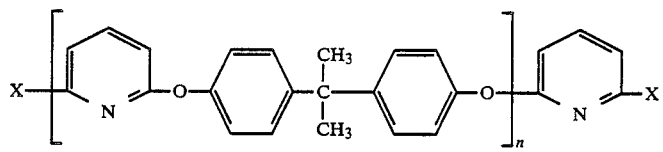

EXAMPLE 16

A mixture of 10.57 grams (0.025 mole) of bis 1,3-(2-bromo 6-pyridyloxy)benzene, prepared as in example 2, with 5.04 grams (0.06 mole) of 2-methyl 3-butyn 2-ol, 0.075 gram (0.1 mmole) of bis(triphenylphosphine)dichloropalladium, 0.4 gram (1.5 mmole) of triphenylphosphine, 0.075 gram (0.395 mmole) of cuprous iodide and 50 cm³ of triethylamine is heated for 6 hours at 110° C. in an argon temperature. The cooled mixture is filtered to remove triethylamine hydrochloride and the solvent is evaporated under reduced pressure. The residue is dissolved in ethyl ether and this solution is washed several times with distilled water. By ether evaporation, a product is obtained with a yield of 66%, which may be identified as bis 1,3-(2-(3-hydroxy 3-methyl butynyl)6-pyridyloxy)benzene, having a melting point of 143° C. and corresponding to the formula:

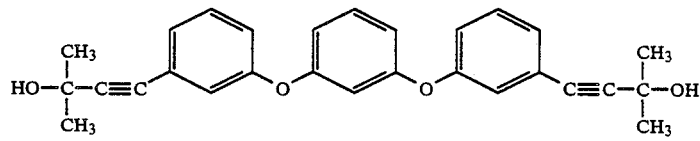

A solution of 3.21 grams (7.5 mmole) of this compound in 35 cm³ of anhydrous toluene is heated to solvent reflux in the presence of 0.5 gram of sodium hydroxide, for 2 hours. The solution is cooled, filtered, and toluene is distilled under reduced pressure. The residue is dissolved in ether, washed several times with water and gives, after evaporation of ether, a solid product whose melting temperature is 100° C. The resultant compound, obtained with a yield of 50%, identified as bis 1,3-(2-ethynyl 6-pyridyloxy)benzene the formula:

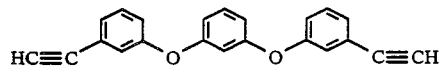

EXAMPLE 17

The experimental conditions of example 16 are used to prepare the bis 2,2-(4-(2-ethynyl 6-pyridyloxyphenyl)propane from the halogenated compound described in example 3.

The obtained compound has a melting temperature of 103° C. and a molecular weight of 430 grams per mole and it complies with the general formula:

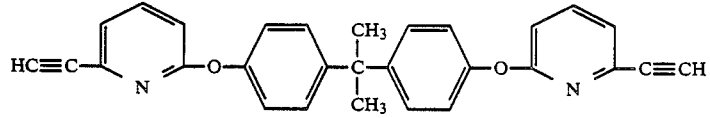

EXAMPLE 18

A mixture of 16.88 grams (0.04 mole) of bis 1,3-(2-bromo 6-pyridyloxy)benzene, obtained as described in example 2, 10 grams (0.1 mole) of ethynyltrimethylsilane, 0.1 gram (0.14 mmole) of bis(triphenylphosphine)-dichloropalladium, 0.3 gram (1.15 mmole) of triphenylphosphine, 0.1 gram (0.5 mmole) of cuprous iodide and 100 cm³ of triethylamine is heated for 7 hours at 50° C. in an autoclave. The cooled mixture is filtered and triethylamine is distilled under reduced pressure.

The residue is dissolved into ether, washed with water and ether is evaporated to give a raw product which is recrystallized in heptane. The yield of pure product is 70%. The obtained compound has a melting temperature of 107° C. and is identified as bis 1,3-(2-(2-trimethylsilyl ethynyl)6-pyridyloxy)benzene complying with the formula:

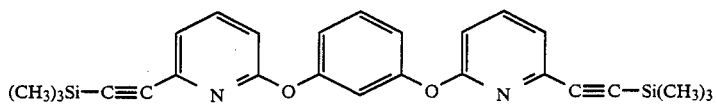

A solution of 2.28 grams (5 mmole) of this compound in 10 cm³ of methanol is stirred at room temperature with 0.56 grams (0.01 mole) of potassium hydroxide, for one hour. After addition of 3N hydrochloric acid aqueous solution (5 cm³), the solution is concentrated under reduced pressure, taken again with ethyl ether and washed several times with water. Ether is evaporated so as to give a raw product which is recrystallized in cyclohexane. The yield of pure product is 50% and its characteristics are identical to those described in example 16.

EXAMPLES 19 TO 21

The experimental conditions of example 18 are used to prepare polyaryloxypyridines with acetylenic end groups from the halogenated compounds described in examples 4, 5 and 6. The analysis of the products obtained by these reactions gives the following results:

EXAMPLE 19

Bis 2,2-(4-(2-ethynyl 6-pyridyloxy)phenyl)propane identical to the compound prepared in example 17.

EXAMPLE 20

Bis 2,2-(4-(2-ethylnyl 6-pyridyloxy)phenyl)1,1,1,3,3,3-hexafluoro propane, having a molecular weight of 538 grams per mole, a melting temperature of 129° C. and complying with the following formula:

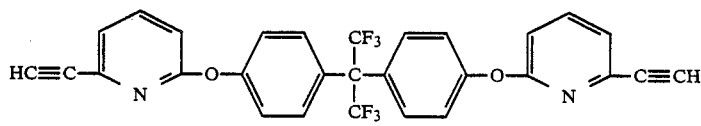

EXAMPLE 21

Bis 4-(2-ethynyl 6-pyridyloxy)phenyl)sulfide, having a melting temperature of 97° C., a molecular weight of 420 grams per mole and corresponding to the formula:

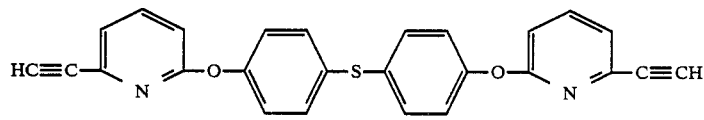

EXAMPLE 22

A mixture of 7 grams of polyaryloxypyridine dibromide as obtained in example 12, with 0.67 gram (6.86 mmole) of ethynyltrimethylsilane, 0.0092 gram (0.0131 mmole) of bis(triphenylphosphine)dichloropalladium, 0.0092 gram (0.048 mmole) of cuprous iodide, 0.0276 gram (0.105 mmole) of triphenylphosphine, 10 cm³ of triethylamine and 40 cm³ of ethyl acetate is heated for 24 hours at 50° C. in an autoclave.

The cooled mixture is filtered and the solvents are distilled under reduced pressure. The residue is crushed in methanol, filtered and dried to obtain a product whose melting point is 86° C. and which corresponds to the formula:

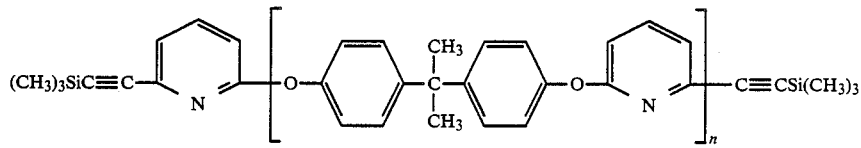

A solution of 2 grams of this product in a mixture of 3 c.c. methanol and 2 c.c. dioxane is stirred at room temperature with 0.1 gram of potassium hydroxide, for one hour, under inert atmosphere. After addition of 1 c.c. of 3N hydrochloric acid aqueous solution, the mixture is concentrated under reduced pressure, then dissolved again in ethyl acetate and washed several times with water.

The organic phase is separated and completely dried by solvent evaporation. The residue is crushed in methanol, filtered and dried. The obtained product has a melting temperature of 71° C., a molecular weight, measured by gel permeation chromatography, of 1748 grams per mole and it may be represented by the following formula of a 2,6-(ethynyl pyridylene) poly(1,4-oxyphenylene(1-methyl ethylidene)-1,4-phenyleneoxy-2,6-pyridylene-ethynyl, wherein n is substantially equal to 5.4.

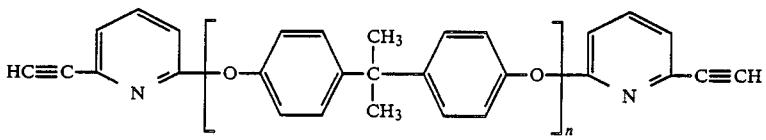

EXAMPLES 23 TO 25

The experimental conditions of example 22 are used to prepare oligomers complying with the above-mentioned formula for an (ethynyl 2,6-pyridylene) poly(1,4-oxyphenylene-(1-methyl ethylidene)1,4-phenyleneoxy 2,6-pyridylene)ethynyl from dihalogenated compounds described in examples 10, 14 and 15. The analysis of the products obtained after fixation of trimethylsilylacetylene and desilylation in a basic medium indicates that the polymers have the following characteristics.

EXAMPLES 23 n=2.5; melting temperature=83° C.; average molecular weight ranging from 890 to 1000 grams per mole.

EXAMPLE 24 n=9; softening temperature=69° C.; average molecular weight ranging from 2900 to 3500 grams per mole.

EXAMPLE 25 n=20; softening temperature=80°-110° C.; average molecular weight ranging from 6200 to 8400 grams per mole.

EXAMPLE 26

Bis 1,3-(2-ethynyl 6-pyridyloxy)benzene prepared in example 16 is subjected to analysis with a differential calorimetry analysis apparatus programmed for a temperature rate of increase of 10° C. per minute.

The thermogram obtained during the first passage shows an endothermic peak of melting at 100° C. and an exothermic peak of polymerization beginning at about 115° C. and ending at about 260° C.

When the product is maintained for 2 hours at 180° C. and then brought back to room temperature, the thermogram obtained by differential calorimetry analysis shows that the melting and polymerization peaks substantially disappeared and at the second passage no slope variation corresponding to a glass transition temperature is observed.

The material obtained after 2 hours of polymerization at 180° C. is subjected to dynamic thermogravimetry analysis with temperature increase rates of respectively 1° to 5° C. per minute. By this method, the thermal stability of the product may be determined with more accuracy since the thermal degradation threshold varies in accordance with the program of temperature increase.

With increasing rates of 1° C. per minute, the decomposition thresholds are respectively at 356° C. in air and 379° C. under argon. With a temperature increase rate of 5° C. per minute the decomposition begins at 402° C. in air and in an inert atmosphere.

When the material is subjected to isothermal thermogravimetric analysis at 300° C. in air, the weight loss is 2.7% after 20 hours in treatment.

EXAMPLES 27 TO 29

The thermal analyses described in example 26 are performed on bis 2,2-(4-(2-ethynyl 6-pyridyloxy)phenyl)propane of example 19, on bis 2,2(4-(2-ethynyl-6-pyridyloxy)phenyl)1,1,1,3,3,3-hexafluoropropane of example 20 and on bis(4-(2-ethynyl 6-pyridyloxy)phenyl)sulfide of example 21.

The results are as follows:

| Example No | 27 | 28 | 29 |
|---|---|---|---|
| Resin of example | 19 | 20 | 21 |
| Melting temperature | 103° C. | 129° C. | 97° C. |
| Beginning of polymerization | 130° C. | 130° C. | 135° C. |
| End of polymerization | 295° C. | 305° C. | 290° C. |
| Glass transition | none | none | none |
| Decomposition threshold in air | 385° C. | 373° C. | 345° C. |
| Decomposition threshold under argon | 390° C. | 394° C. | 360° C. |

EXAMPLES 30 TO 32

The thermal analyses are performed on oligomers of higher molecular weight whose synthesis is described in examples 22, 23 and 24, with the following results.

| Example No | 30 | 31 | 32 |
|---|---|---|---|
| Resin of example | 22 | 23 | 24 |
| DPn of the resin | 5.4 | 2.5 | 9 |
| Beginning of polymerization | 135° C. | 130° C. | 135° C. |
| End of polymerization | 290° C. | 285° C. | 290° C. |
| Glass transition: | | | |
| after 2 hours at 180° C. | 94° C. | 116° C. | 88° C. |
| after 16 hours at 250° C. | 113° C. | 140° C. | 109° C. |
| Decomposition threshold in air | 297° C. | 344° C. | 295° C. |
| Decomposition threshold under argon | 297° C. | 365° C. | 295° C. |

EXAMPLE 33

A mixture of 14.22 grams (0.060 mole) of 3,5-dibromopyridine, 4.56 grams (0.020 mole) of bis 2,2(4-hydroxyphenyl)propane, 6.35 grams of potassium carbonate, 0.22 gram of cuprous chloride, 0.16 gram of potassium iodide, 80 cm³ de N-methyl 2-pyrolidinone and 40 cm³ of toluene is heated at 144° C. with azeotropic removal of the water formed during the reaction. The heating time which is 8.5 hours, is determined by the complete disappearance of the phenol groups. After cooling, the reaction mixture is filtered and the filtrate is concentrated by distillation under reduced pressure of the major part of the solvents. The residue is poured into water and the formed precipitate is washed with water and dried. It is then taken again in 50 cm³ of ethyl acetate. The solution is filtered to remove impurities insoluble in ethyl acetate. After solvent evaporation, the residue is extracted with 250 cm³ of boiling hexane. This operation gives two fractions. The first one is soluble into hexane whereas the second gives an immiscible phase.

The fraction soluble in hexane is separated by solvent evaporation and extensive drying at 100° C. under reduced pressure. The separated product consisting of a clear yellow oil weighs 4.38 grams (yield of 41%) and complies with the formula:

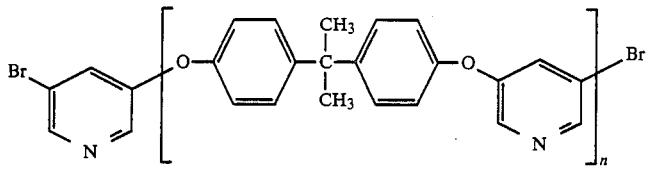

The gel permeation chromatography analysis of this product shows that it is formed of oligomers corresponding to the preceding formula with 84% of compound for which the polycondensation degree n is equal to 1, 11% of oligomer for which n is equal to 2 and 5% of unidentified compound having an apparent molecular weight of 370 grams.mole$^{-1}$.

The fraction insoluble in hexane appears as a brown viscous oil and amounts to 3.11 grams. The chemical, spectroscopic and chromatographic analyses indicate that it is formed of oligomers complying with the preceding formula, with the following distribution: 29% of oligomers n=1, 34% of oligomers n=2, 20% of oligomers n=3 and 17% of higher oligomers.

EXAMPLE 34

A mixture of 8.66 grams of the first fraction prepared in example 33, essentially consisting of bis 2,2-(4-(3-bromo 5-pyridyloxy)phenyl)propane corresponding to 31.7 milliequivalents of bromine, 3.3 grams (0.0396 mole) of 2-methyl 3-butyn 2-ol, 44 milligrams of bis(triphenylphosphine)dichloropalladium, 0.249 gram of triphenylphosphine, 46 milligrams of cuprous iodide and 60 cm$^3$ of triethylamine is heated for 5 hours at 110° C. in a nitrogen atmosphere. After cooling, the mixture is filtered and the precipitate is rinsed with ethyl ether. The fractions insoluble in ether are joined to the filtrate. After evaporation of the solvents, the residue is dissolved in 40 cm$^3$ of boiling ethanol. After filtration of the hot ethanol solution, and water addition, up to the formation of a persistent turbidity, the mixture is allowed to settle. A solid is formed which is separated by filtration and recrystallized from toluene. The yield of dry product is 5.69 grams (65%). The analysis shows that this product complies with the formula:

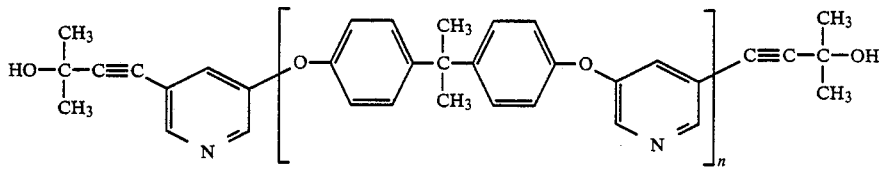

wherein the polycondensation degree is equal to 1.05.

EXAMPLE 35

A mixture of 3.06 grams of oligomers prepared in example 34, mainly consisting of bis 2,2-(4-(3-(3-hydroxy 3-methylbutynyl)5-pyridyloxy)phenyl)propane, 0.34 gram of sodium hydroxide powder and 50 cm$^3$ of toluene is heated for 210 minutes at 111° C. in a nitrogen atmosphere. A fraction of the solvent, corresponding to about 12 cm$^3$, is slowly distilled during the reaction so as to remove the formed acetone. After cooling, the solution is filtered and washed with water to give, after evaporation of toluene under reduced pressure and extensive drying in vacuum, 1.91 grams of a viscous oil. The analysis of this product shows that it corresponds to the formula:

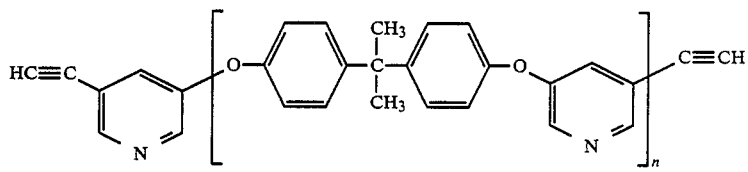

The gel permeation chromatography analysis of this product shows that it is formed of oligomers complying with the preceding formula with 92% of the compound for which the polycondensation degree n is equal to 1 and 8% of oligomer for which n is equal to 2.

EXAMPLE 36

A mixture of 37.92 grams (0.16 mole) of 3,5-dibromopyridine, 18.24 grams (0.08 mole) of bis 2,2-(4-hydroxyphenyl)propane, 14.35 grams of potassium carbonate, 0.88 grams of cuprous chloride, 0.65 gram of potassium iodide, 260 cm$^3$ of N-methyl 2-pyrrolidinone and 130 cm$^3$ of toluene is heated for 2 hours at 144° C. with azeotropic removal of the water formed during the reaction. The distilled toluene is then progressively removed from the Dean and Stark settler in 5 hours, the temperature of the reaction mixture increasing progressively from 144° C. to 156° C. The temperature is then increased up to 180° C. in 2 hours. After cooling, the reaction mixture is filtered and the filtrate is washed with chloroform and then refiltered.

The product obtained by distillation of the solvents under reduced pressure is then taken again with 150 cm$^3$ of ethyl acetate. The solution is filtered to remove impurities insoluble in ethyl acetate. It is then percolated over 30 grams of gel of silica particles having a 0.08 mm average diameter. The solvent evaporation gives a yellow spongy product with a yield of 46%. The gel permeation chromatography analysis of this product shows that it is formed of oligomers complying with the formula of example 33, with 46% of compound for which the polycondensation degree n is equal to 1, a proportion of 51% of oligomers for which n is at least 2, and 5% of an unidentified compound having an apparent molecular weight of 370 grams.mole$^{-1}$. The determination of bromine atoms constituting the end groups indicates that the average value of the polycondensation degree n is 1.99.

EXAMPLE 37

A mixture of 19.82 grams of the dibrominated product prepared in example 36, corresponding to 47.2 bromine milliequivalents, with 4.94 grams of 2-methyl 3-butyn 2-ol, 66 milligrams of bis(triphenylphosphine)dichloropalladium, 0.376 grams of triphenylphosphine, 69 milligrams of cuprous iodide and 88 cm$^3$ of triethylamine is heated for 270 minutes at solvent reflux in a nitrogen atmosphere. After cooling, the mixture is filtered and washed with water. After evaporation of the solvents, the gummy residue is dissolved in 40 cm$^3$ of boiling ethanol. After filtration of the hot ethanol solution, an addition of water up to the formation of a persistent turbidity, the mixture is allowed to settle. A viscous phase is formed and settles at the bottom of the vessel. This phase is separated and dried under vacuum. The yield of dry product is 15.02 grams (75%). The analysis of this product shows that it complies with the general formula of example 34 with an average polycondensation degree n of 2.

A solution of 13.5 grams of this product into 150 cm$^3$ of toluene is heated at 111° C. in the presence of 1.4 gram of sodium hydroxide powder, for 5 hours. A fraction of the solvent, corresponding to about 37 cm$^3$, is slowly distilled during the reaction so as to remove the formed acetone. After cooling, the solution is filtered, washed with water and gives, after evaporation of toluene under reduced pressure and an extensive drying under vacuum, 8.54 grams of a viscous oil. The analysis of this product shows that it complies with the general formula of example 35 wherein the polycondensation degree, determined by elementary analysis and by nuclear magnetic resonance, has an average value of 2.5.

EXAMPLE 38

The polycondensation of 3,5 dibromopyridine with Bis 2,2-(4-hydroxphenyl)propane is performed in the experimental conditions described in example 36, with the use of a molar ratio between these two reactants of 1.5. The product obtained at the end of the reaction is a solid corresponding to the general formula of example 33. The analysis of this product by gel permeation chromatography shows that it is formed of oligomers of polyaryloxypyridines ending with bromine atoms, with 29% of the product for which the polycondensation degree n is equal to 1, a proportion of 67% of oligomers for which n is at least 2 and 4% of an unidentified compound having an apparent molecular weight of 370 grams.mole$^{-1}$. The bromine determination indicates an average value of 3.37 for the polycondensation degree n.

EXAMPLE 39

The oligomer mixture prepared in example 38 is reacted with 2-methyl 3-butyn 2-ol in the conditions described in example 37. This operation results in the substitution of bromine atoms with protected acetylenic groups, with a yield of 52%. The further treatment of 5.76 grams of the latter product with 0.5 gram of sodium hydroxide in 80 cm$^3$ of toluene gives 4.29 grams (82%) of a brown-colored very viscous oil, corresponding to the general formula of example ±wherein the average polycondensation degree n is 3.3.

EXAMPLE 40

The polycondensation reaction of 3,5 dibromopyridine with bis 2,2-(4-hydroxyphenyl)propane is performed in the experimental conditions described in example 36, with a molar ratio of 1.15 between these two reactants. The product obtained at the end of the reaction, with a yield of 42%, is a solid whose analysis by gel permeation chromatography shows that it is formed of oligomers complying with the general formula of example 33, with 11 % of compound for which the polycondensation degree n is equal to 1 and 89% of oligomers for which n is at least 2.

This product, dissolved in chloroform, is precipitated in methanol to give a solid containing more than 6.5% of oligomer for which n is equal to 1. The determination of bromine atoms and the elementary analysis indicate that the average polycondensation degree n is equal to 11, corresponding to an average number molecular weight close to 3,500 grams.mole$^{-1}$.

This mixture of dibrominated polyaryloxypiridines is subjected to dynamic thermogravimetric analysis in nitrogen atmosphere with a rate of temperature increase of 10° C. per minute. The thermal decomposition threshold is at about 260° C. and the weight loss reaches 1% at 350° C. and 5% at 410° C.

EXAMPLE 41

The fraction of dibrominated polyaryloxypiridine oligomer soluble in ethyl acetate but insoluble in hexane, separated in example 33, is treated as in example 39 to give, with a yield of 40%, a viscous liquid corresponding to the general formula of example 35.

The analysis of this product by gel permeation chromatography shows that it is formed of oligomers containing 42% of compound for which the polycondensation degree n is equal to 1, a proportion of 33% of oligomer for which n is equal to 2 and 24% of oligomers having a polycondensation degree of at least 3. The bromine determination, elementary analysis and nuclear magnetic resonance indicate that the average polycondensation degree has a value of 1.7 but with a widened range of molecular weight distribution as compared with the oligomers described in examples 35, 37 and 39.

EXAMPLE 42

The thermal characteristics of the oligomers prepared in example 35 are surveyed by means of a differential calorimetry analysis apparatus programmed for a temperature rate of increase of 10° C. per minute. The thermograms are drawn within 20°–270° C. During the first temperature increase, the thermogram shows an exothermal polymerization peak beginning at 145° C., having a a maximum value at 242° C., and ending at about 300° C. No other thermal transition is observed before this polymerization peak. After cooling of the measuring cell, a second temperature increase shows that the polymerization peak has disappeared and that no variation of the thermogram slope which might indicate the presence of glass transition is observed.

From these data, a material is prepared by polymerizing a few grams of the oligomer composition of example 35 in a metal cup during 2 hours at 180° C.

The lattice obtained during this thermal polymerization reaction is then subjected to dynamic thermogravimetry analysis in air with a temperature increase rate of 5° C. per minute. The degradation threshold of the product occurs at 420° C. and the weight loss is 1% at 440° C. and 5% at 450° C.

EXAMPLE 43

The thermal analyses described in example 42 are performed with the oligomers described in examples 37, 39 and 41 with the following results:

| Resin of example | 37 | 39 | 41 |
|---|---|---|---|
| DPn of the resin | 2.5 | 3.3 | 1.7 |
| Beginning of polymerization | 140° C. | 180° C. | 140° C. |
| Maximum of the exotherm | 245° C. | 225° C. | 237° C. |
| End of polymerization | 305° C. | 295° C. | 310° C. |
| Glass transition (at second passage) | 120° C. | 123° C. | none |
| 1% of decomposition in air | 406° C. | 350° C. | 415° C. |
| 5% of decomposition in air | 434° C. | 415° C. | 460° C. |

What is claimed as the invention is:

1. An oligomer composition of polyaryloxypyridine having acetylenic end groups, obtained by formation of a composition of polyaryloxypyridine by halogenated end groups from at least one alkaline diphenolate and at least one dihalogenopyridine, followed with an ethynylation reaction.

2. A composition according to claim 1, characterized in that it is represented by the general formula:

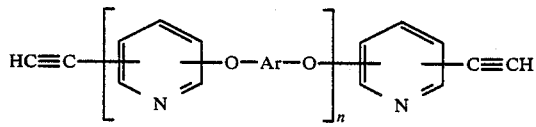

wherein Ar is a divalent aromatic, carbocyclic or heterocyclic radical formed of one or more rings, fused or interconnected through a single bond or through a divalent atom or group, the two valences of said aromatic radical Ar being placed on two separate carbon atoms, n being the average polycondensation degree.

3. A composition according to claim 2, wherein said average polycondensation degree ranges from 1 to 50.

4. A process for manufacturing an oligomer composition according to claim 1, characterized by the steps of
 (a) preparing a composition of polyaryloxypyridine with halogenated end groups by a method consisting of:
  (i) preparing an alkaline diphenolate by reacting a diphenol with an alkaline reactant, selected from alkali metals, their hydroxides, their carbonates and alcoholates, and
  (ii) reacting the obtained alkali diphenolate with a dihalogenopyridine, the molecular amount of said alkaline diphenolate being stoichiometrically with respect to said dihalogenopyridine, so as to obtain an oligomer composition of polyaryloxy pyridine with halogenated end groups, which is separated from the reaction medium, and
 (b) converting said oligomer composition of polyaryloxypyridine with halogenated end groups to a polyaryloxypyridine composition with acetylenic end groups by a method consisting of:
  (iii) reacting said oligomer composition of polyaryloxypiridine with halogenated end groups with at least one acetylenic compound, one of the reactive sites of which is protected by a protecting group, so as to form substituted acetylenic end groups, and
  (iv) converting said substituted acetylenic end groups to free acetylenic end groups.

5. A process according to claim 4, wherein in step (a)(i), the molar ratio of alkaline diphenolate to dihalogenopyridine is from 1/1.02 to 1/2 and the reaction is performed at a temperature from 50° to 300° C.

6. A process according to claim 4, wherein, in step (b)(iii), said acetylenic compound has the formula:

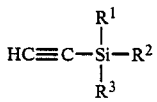

or:

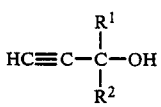

7. A process according to claim 4, wherein, in step (b)(iii), the reaction is conducted in solution in an organic solvent, in the presence of a basic compound capable of fixing hydracid molecules and in the presence of a catalytic system comprising a copper compound and a palladium compound, at a temperature from 20° to 200° C.

8. A process according to claim 7, wherein said copper compound is a cuprous compound and said palladium compound is: Pd(PR$_3$)$_4$, Pd(PR$_3$)$_2$X$_2$, Pd(O$_2$CR)$_2$(PR$_3$)$_2$, Pd(O$_2$CR)$_2$ or Pd(AsR$_3$)$_2$X$_2$ wherein X is a halogen atom and R is an alkyl, aralkyl or aryl group.

9. A process according to claim 4, wherein the acetylenic compound used in step (b)(iii) is a compound of the formula

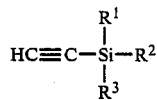

wherein each of R$^1$, R$^2$ and R$^3$ represents a monovalent aliphatic or aromatic residue having 1 to 13 carbon atoms and, in step (b)(iv) the desilylation reaction is conducted in solution in an aliphatic monoalcohol in the presence of an inorganic base at a temperature from 50° to 150° C.

10. A process according to claim 4, wherein the acetylenic compound used in step (b)(iii) is a compound of the formula:

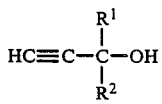

wherein each of $R^1$ and $R^3$ represents a monovalent aliphatic or aromatic residue having from 1 to 13 carbon atoms, and step (b)(iv) comprises the removal of the ketone of formula $R^1$—CO—$R^2$, in solution in an organic solvent, in the presence of an inorganic base and at a temperature from 50° to 150° C.

11. A process for the production of crosslinked polymers from an oligomer composition of polyaryloxypyridine with acetylenic end groups, comprising heating said composition to a temperature from 100° to 250° C. to form cross-linked solid polymers.

12. A process according to claim 11, wherein the heating is subsequently continued at a temperature from 200° to 300° C.

13. A cross-linked polymer produced by a process according to claim 11.

14. A process according to claim 11, wherein the oligomer composition has the formula

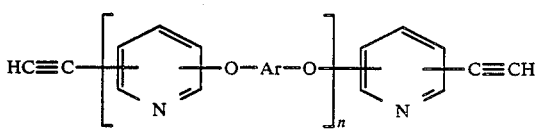

wherein Ar is a divalent aromatic, carbocyclic or heterocyclic radical formed of one or more rings, fused or interconnected through a single bond or through a divalent atom or group, the two valences of said aromatic radical Ar being placed on two separate carbon atoms, n being the average polycondensation degree.

* * * * *